US009375188B2

(12) United States Patent
Schmidt

(10) Patent No.: US 9,375,188 B2
(45) Date of Patent: Jun. 28, 2016

(54) METHOD AND DEVICE FOR IMPROVING MEDICAL IMAGE DATA AND EVALUATION OF TISSUE CONTENT WITHIN THE MEDICAL IMAGE DATA

(75) Inventor: Sebastian Schmidt, Weisendorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 265 days.

(21) Appl. No.: 13/182,597

(22) Filed: Jul. 14, 2011

(65) Prior Publication Data

US 2012/0016225 A1  Jan. 19, 2012

(30) Foreign Application Priority Data

Jul. 15, 2010  (DE) .......................... 10 2010 027 277

(51) Int. Cl.
*A61B 5/05* (2006.01)
*A61B 6/03* (2006.01)
*A61B 5/055* (2006.01)
(Continued)

(52) U.S. Cl.
CPC ............. *A61B 6/037* (2013.01); *A61B 5/055* (2013.01); *A61B 6/4417* (2013.01); *A61B 6/50* (2013.01); *A61B 6/5247* (2013.01);
(Continued)

(58) Field of Classification Search
CPC ............. G01R 33/4828; G01R 33/481; A61B 5/4872; A61B 5/055; A61B 5/4875; A61B 6/037; A61B 6/4417; A61B 6/5247; A61B 6/50
USPC ............... 600/410, 411; 382/131; 250/363.01
See application file for complete search history.

(56) References Cited

U.S. PATENT DOCUMENTS 7,286,867 B2 * 10/2007 Schlyer et al. ............... 600/407
7,378,660 B2 *  5/2008 Case et al. ............... 250/363.01
(Continued)

FOREIGN PATENT DOCUMENTS

DE  102008044844 A1  3/2010

OTHER PUBLICATIONS

Positronen-Emissions-Tomographie. In: Wikipedia, Die freie Enzyklopädie. Bearbeitungsstand: Jul. 9, 2010, 09:55. URL: http://de.wikipedia.org/w/index.php?title=Positronen-Emissions-Tomographie&oldid=76476369 [abgerufen am Mar. 10, 2011]; Others; 2010.

(Continued)

*Primary Examiner* — Long V Le
*Assistant Examiner* — Helene Bor
(74) *Attorney, Agent, or Firm* — Harness, Dickey & Pierce, P.L.C.

(57) ABSTRACT

A method is disclosed for recording and displaying medical imaging data records of a body part including fatty tissue. In at least one embodiment, the method includes recording an emission-tomographic data record of the body part; recording a magnetic-resonance imaging data record of the body part using a recording sequence designed such that fatty tissue can be displayed such that it can be distinguished from other types of tissue; identifying regions in the emission-tomographic data record, which regions correspond to fatty tissue, using the magnetic-resonance imaging data record; and modifying the emission-tomographic data record in those regions that correspond to fatty tissue. Further, at least one embodiment relates to a correspondingly designed device for evaluating and displaying medical imaging data records of a body part comprising fatty tissue.

13 Claims, 3 Drawing Sheets

(51) Int. Cl.
*A61B 6/00* (2006.01)
*G01R 33/48* (2006.01)
*A61B 5/00* (2006.01)

(52) U.S. Cl.
CPC ............ *G01R 33/481* (2013.01); *A61B 5/0035* (2013.01); *G01R 33/4828* (2013.01)

(56) References Cited

U.S. PATENT DOCUMENTS

| | | | |
|---|---|---|---|
| 8,781,197 B2 * | 7/2014 | Wang et al. | 382/131 |
| 2005/0113667 A1 * | 5/2005 | Schlyer et al. | 600/411 |
| 2006/0025673 A1 * | 2/2006 | De Leon et al. | 600/410 |
| 2008/0135769 A1 | 6/2008 | Rosen | |
| 2010/0052674 A1 | 3/2010 | Jellus | |
| 2010/0204563 A1 * | 8/2010 | Stodilka et al. | 600/411 |
| 2011/0058722 A1 * | 3/2011 | Hu et al. | 382/131 |
| 2012/0076378 A1 * | 3/2012 | Keereman et al. | 382/131 |

OTHER PUBLICATIONS

German Priority Document DE 10 2010 027 277.9, not yet published.

* cited by examiner

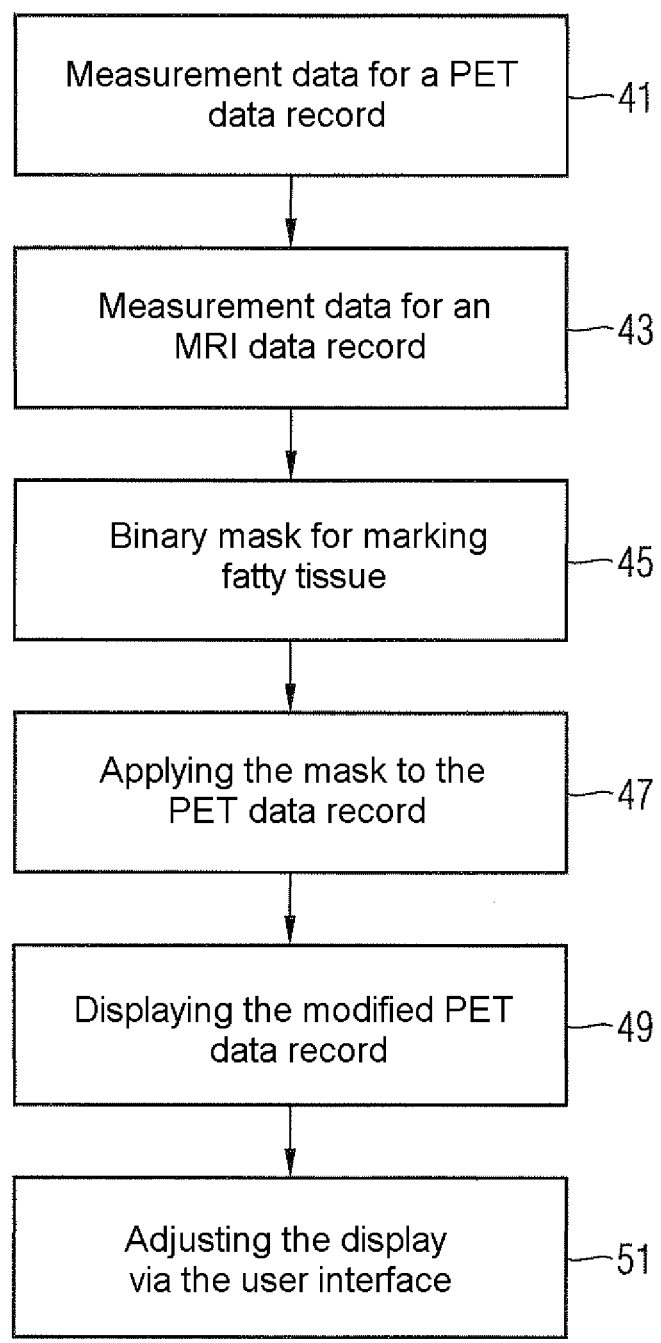

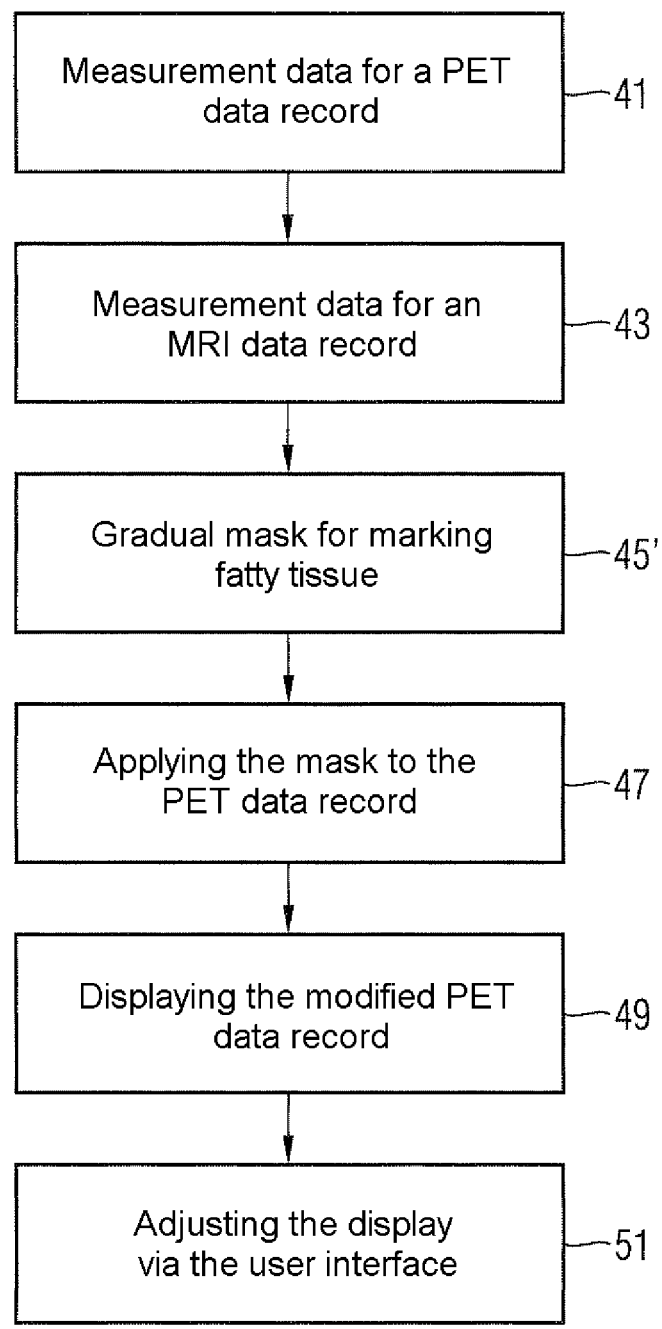

METHOD AND DEVICE FOR IMPROVING MEDICAL IMAGE DATA AND EVALUATION OF TISSUE CONTENT WITHIN THE MEDICAL IMAGE DATA

PRIORITY STATEMENT

The present application hereby claims priority under 35 U.S.C. §119 on German patent application number DE 10 2010 027 277.9 filed Jul. 15, 2010, the entire contents of which are hereby incorporated herein by reference.

FIELD

At least one embodiment of the invention generally relates to a method for recording and displaying medical imaging data records of a body part comprising fatty tissue. At least one embodiment of the invention furthermore relates to a device for evaluating and displaying medical imaging data records that image a body part comprising fatty tissue. Such imaging data records may be generated by positron emission tomography scanners (referred to as PET scanners below) and magnetic resonance imaging scanners (referred to as MRI scanners below) in particular.

BACKGROUND

So-called positron emission tomography (also abbreviated to PET) is used during medical examinations to image the metabolic activity of a body part. PET recordings allow conclusions to be drawn in respect of which regions in the body have a particularly active metabolism. From this, it is possible to obtain clues as to whether certain body regions exhibit pathological change, for example as a result of a malignant growth process.

Magnetic resonance imaging (also abbreviated to MRI) is also known; it is used during medical examinations to obtain images that reproduce the anatomical conditions in a body part.

Furthermore, combined MRI/PET scanners are known, which can be used to carry out both imaging modalities matched to one another. A combined display of MRI images and PET images allow conclusions to be drawn both in respect of anatomical conditions and functional processes within the body.

SUMMARY

In at least one embodiment of the invention, a method is specified for recording and displaying medical imaging data records of a body part containing fatty tissue, which helpfully assists a user in the evaluation of the data records. Furthermore, at least one embodiment of the invention specifies a device for evaluating and displaying such imaging data records, which device allows a user to evaluate the imaging data records in a convenient fashion.

Advantageous developments of the invention can be found in the features of the dependent claims.

The method according to at least one embodiment of the invention for recording and displaying medical imaging data records of a body part comprising fatty tissue comprises:

recording an emission-tomographic data record of the body part,
recording an MRI data record of the body part using a recording sequence designed such that fatty tissue can be displayed such that it can be distinguished from other types of tissue,
identifying regions in the emission-tomographic data record, which regions correspond to fatty tissue, using the MRI data record, and
modifying the emission-tomographic data record in those regions that correspond to fatty tissue.

At least one embodiment of the invention is based on the discovery that in emission-tomographic recordings, such as e.g. PET recordings in which glucose metabolism processes are imaged (e.g. FDG [18F-fluorodeoxyglucose] PET recordings), fatty tissue normally displays no or only very little activity because the glucose metabolism is low in the fatty tissue. However, at least one embodiment of the invention is not necessarily restricted to PET recordings. By way of example, an application using other emission-tomographic recordings, such as e.g. SPECT, is also feasible.

However, at least one embodiment of the invention is also based on the deliberation that this does not necessarily hold true in a specific type of fatty tissue, which is known as brown (or else plurivacuolar) fatty tissue. This form of fatty tissue can directly convert energy into heat. Brown fatty tissue can have a significant glucose metabolism, particularly if it is cold. Brown fatty tissue mainly exists in newborns where it serves to produce heat because the heat production by muscles is too low to keep the body warm in a newborn as a result of the low muscle mass. However, occasionally there also is brown fatty tissue in children and relatively young patients (particularly in women).

It was discovered that precisely this brown fatty tissue can cause significant misdiagnoses in the findings of an emission-tomographic examination. Thus, by way of example, brown fatty tissue stored in e.g. the region of the neck can feign malignant lymph nodes, e.g. in the case of lymphomas or head-neck tumors. In a PET examination or a PET/computed-tomography examination, it is virtually impossible to identify whether FDG activity was caused by lymph nodes or brown fatty tissue.

This is particularly dangerous because this phenomenon occurs only scarcely. Moreover, the brown fatty tissue activity is dependent on the temperature. Therefore this phenomenon mainly occurs in cold weather and only in specific patients as well. The converse error is also possible: malignant lesions could erroneously be considered to be benign brown fatty tissue.

It was also identified that up until now this problem could only be countered in an insufficient fashion. A user diagnosing the images must constantly bear this effect in mind and, if necessary, introduce other measures such as a biopsy that allow a definite answer. However, such measures are complicated and are a burden for the patient.

At least one embodiment of the invention is developed on the basis of these deliberations. It was identified that magnetic resonance imaging is particularly suitable for supplementing the missing information.

To this end, an MRI data record is recorded of the body part, to be precise with a recording sequence that is suitable for marking fatty tissue. This means that those voxels in the recorded MRI data record that image fatty tissue can be distinguished from other types of tissue. The information obtained by the MRI data record can be used to identify those regions in the emission-tomographic data record that correspond to fatty tissue.

The emission-tomographic data record can thereupon be modified to the extent that those regions that correspond to fatty tissue are processed and/or illustrated differently, in contrast to regions that correspond to other types of tissue.

As a result of this, a user can be assisted to the effect that he/she can easily identify when there is increased metabolic activity in the fatty tissue. These circumstances are a strong indication that brown fatty tissue was the cause. Thus, the user is assisted to the effect that the relevance of emission-tomographic signals is assessed. This allows clarification in respect of the cause of metabolic activities with the aid of imaging methods that cause less discomfort to the patient.

The recording sequence can be a recording sequence or a pulse sequence in which voxels in the imaging data record are characterized by intensity values, with the intensity values constituting a measure for the fat content of the body regions that correspond to the voxels.

Appropriate techniques are known in magnetic resonance imaging. They are used, for example, to separate fat and water. By way of example, use can be made of spectral methods or methods that utilize the phase difference. An example for this is the known Dixon MRI technique.

Such methods are usually applied to suppress fat, but they can conversely likewise be used to obtain an image that mainly images fatty tissue and largely suppresses water. Hence, this results in a data record that images the fat content for each voxel.

In one embodiment, the MRI data record and the emission-tomographic data record are recorded with temporal overlap or directly one after the other, more particularly with a hybrid emission-tomography/magnetic-resonance scanner. The MRI data record and the emission-tomographic data record can be recorded with the same positioning of the patient.

This means that the emission-tomographic data is already recorded, at least in part, while the MRI measurement data is being recorded. However, it is also feasible for the emission-tomographic data to be recorded immediately before or after the MRI measurement data is recorded.

The examination with both imaging modalities can take place during the same examination session. Thus, it is not necessary to reposition the patient; the patient may be left on the examination table. As a result, a relation between the voxels of the emission-tomographic data record and the MRI data record is known. Even the examination table may remain at the same position within the scanner without having to be displaced. What this achieves is that the voxels of the emission-tomographic data record and the magnetic-resonance imaging data record, which correspond to one another, are not offset with respect to one another.

In one embodiment, the emission-tomographic data record can be modified using a mask generated from the MRI data record. The mask is used to mark regions of fatty tissue.

Using a mask allows simple marking and characterization of those regions in the emission-tomographic data record that correspond to fatty tissue. Thus, by way of example, the emission-tomographic signal of voxels that mainly contain fat can be set to zero or can be attenuated. In this case, the result is an emission-tomographic data record that now only contains signals from voxels that do not predominantly contain fatty tissue. Assessments are simplified by virtue of the fact that the emission-tomographic signals that originate from usually uncritical regions are reduced or even masked.

The mask can be a binary mask. A threshold can be used to distinguish between voxels, which as a result are characterized as either voxels of fatty tissue or voxels of non-fatty tissue.

In another embodiment the mask can be a gradual mask with a plurality of mask values, with the mask values of the mask correlating with the fat content of corresponding voxels in the MRI data record.

The plurality of mask values can then be used to attenuate the emission-tomographic signal of the voxels in the emission-tomographic data record in accordance with the mask values. This gradually masks emission-tomographic signals, to be precise according to the fat content of the corresponding voxels. A user can use a user interface, for example, to switch the "fat suppression" on or off. It is possible to show the user whether the fat suppression is activated or switched off. By way of example, a user can also be provided with the option of masking the voxels containing fat in the emission-tomographic data record continuously to a greater or lesser degree by way of a slider or the like.

The step of modifying the emission-tomographic data record may comprise marking fatty-tissue regions in the emission-tomographic data record, which marking is carried out using the MRI data record. More particularly, the marking may comprise an attenuation of the emission-tomographic signal in fatty-tissue regions compared to non-fatty-tissue regions.

However, the attenuation of voxels that correspond to fatty tissue is only one option for marking the voxels. Other types of marking are also feasible, for example colored labeling, bordering or the like.

The device according to at least one embodiment of the invention for evaluating and displaying medical imaging data records of a body part comprising fatty tissue comprises:
a computer unit, which is designed to
  provide an emission-tomographic data record of the body part,
  provide an MRI data record of the body part, which was recorded by a recording sequence designed such that fatty tissue can be displayed such that it can be distinguished from other types of tissue,
  identify regions in the emission-tomographic data record that correspond to regions of fatty tissue, using the MRI data record, and
  modify the emission-tomographic data record in those regions that correspond to fatty tissue.

The device can be designed to carry out one of the methods described in more detail above; in particular, the data records can be processed according to the methods explained in more detail above.

The computer unit can be a component of a hybrid emission-tomography/magnetic-resonance scanner, which comprises an emission-tomography unit for recording the emission-tomographic data record and a magnetic-resonance unit for recording the magnetic-resonance imaging data record.

The preceding and the following description of the individual features, the advantages thereof, and the effects thereof relate both to the device category and to the method category without this being explicitly mentioned in detail in each case; the individual features disclosed thereby can also be essential to the invention in combinations that differ from those illustrated.

BRIEF DESCRIPTION OF THE DRAWINGS

Embodiments of the invention with advantageous developments as per the features of the dependent claims are explained in more detail on the basis of the following drawing, without, however, being restricted thereto. In detail:

FIG. 2 shows a schematic flowchart of one embodiment of the method according to the invention, and FIG. 3 shows a further embodiment of the method.

DETAILED DESCRIPTION OF THE EXAMPLE EMBODIMENTS

Figure 1:
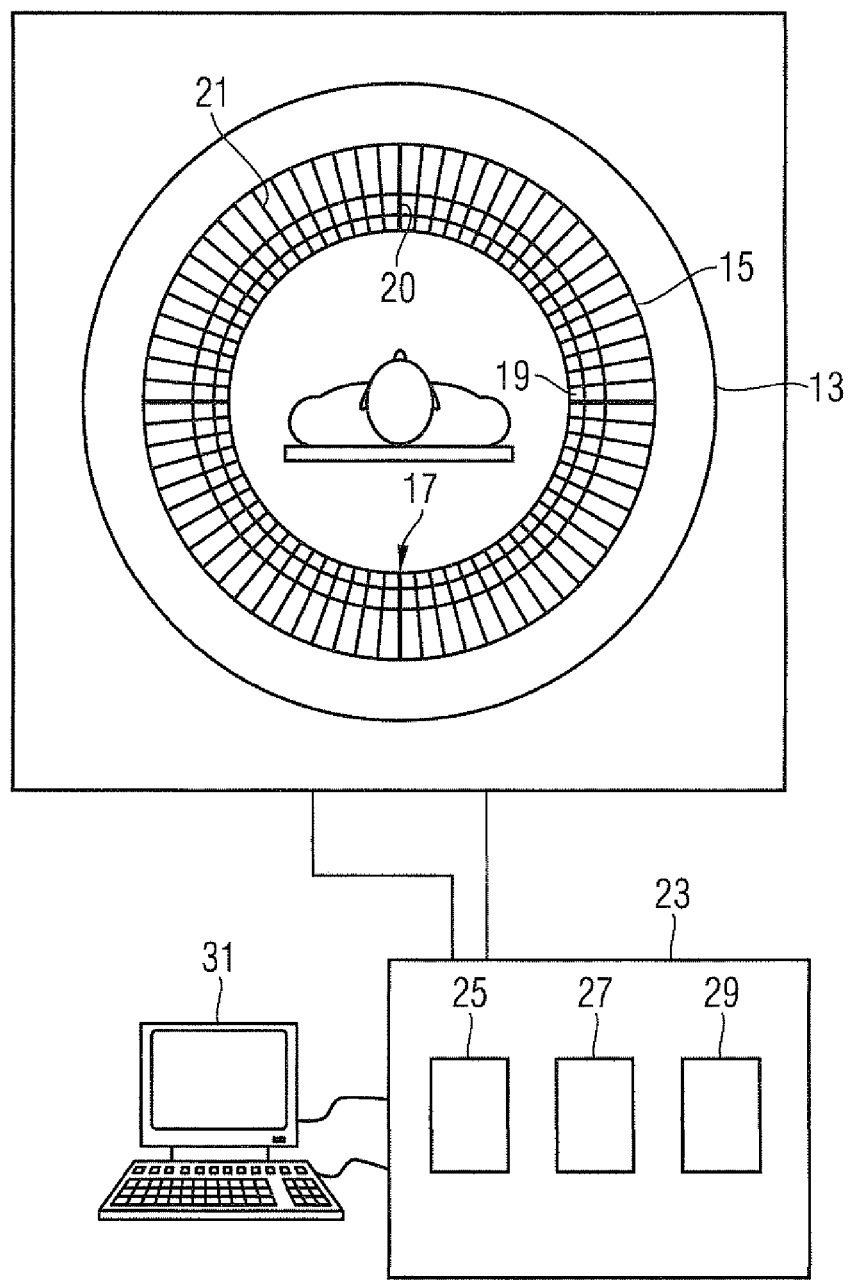
FIG. 1 shows a schematic illustration of an MRI/PET scanner that is designed for recording, processing, and displaying combined magnetic-resonance/PET images.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a known combined MRI/PET scanner 11 that is used in an example embodiment of the invention. An advantage of the combined MRI/PET scanner is that both MRI and PET data can be obtained isocentrically. Moreover, the measurement data can be recorded at the same time.

In principle, parallel recording can also be undertaken if the MRI/PET scanner does not have an isocentric design. In this case, measurement data can be recorded simultaneously with both modalities, respectively for different regions.

The MRI/PET scanner 11 comprises a known tubular MRI unit 13. The MRI unit 13 is only indicated schematically and defines a longitudinal direction z, which extends orthogonally to the plane of the drawing in FIG. 1.

As shown in FIG. 1, a PET unit 15 is arranged coaxially within the MRI unit 13. Said PET unit comprises a plurality of PET detection units 17, arranged opposite one another in pairs about the longitudinal direction z. The PET detection units 17 preferably consist of an APD photodiode array 20 with an upstream array made of LSO crystals 19 and an electric amplifier circuit 21. However, at least one embodiment of the invention is not restricted to the PET detection units 17 with the APD photodiode array 20 and the upstream array of LSO crystals 19; differently designed photodiodes, crystals, and devices can likewise be used for the purposes of detection.

During an MRI and/or PET examination, a patient to be examined is successively moved to different positions by way of a patient table in order in each case to move the section to be examined into the examination region (field of view) of the MRI unit 13 and/or the PET unit 15.

The MRI/PET scanner 11 is controlled by a control device 23. The control device 23 can for example comprise a first partial apparatus 25 for controlling the MRI unit 13 and a second partial apparatus 27 for controlling the PET unit 15 for carrying out the PET measurement data recording. The first partial apparatus 25 and/or the second partial apparatus 27 can likewise actuate the patient table and position it correctly. Furthermore, the control device 23 can comprise an evaluation computer 29, which is connected to the partial apparatuses 25, 27, analyzes the recorded measurement data and is able to generate a hybrid image 31 of the examination object. The hybrid image 31 can be displayed to a user or stored in a storage medium. The components of the control device 23 are interconnected.

Such a device is known from the prior art.

The control device 23 with its units 25, 27, 29 is developed such that the method described below on the basis of FIG. 2 and FIG. 3 can be carried out.

FIG. 2 shows a flowchart of an embodiment of the method according to an embodiment of the invention.

The measurement data for a PET data record and for an MRI data record is recorded on a patient who was administered FDG glucose before the recording. This glucose is metabolized in the body of the patient and generates a signal at metabolizing points in the body of the patient, which signal can be recorded by the PET unit (step 41).

An MRI data record is recorded at the same time as the recording of the PET signals, or directly before or after this, without the patient being repositioned (step 43).

A fat-sensitive MRI sequence is used to record the MRI data record. This means that it is possible to use the recorded MRI measurement data to generate an image in which the intensity values of the voxels characterize the fat content of the corresponding regions in the body and/or in which regions of fatty tissue can be displayed such that they can be distinguished from other types of tissue.

Subsequently, using the MRI data record, a mask is generated by means of which regions of fatty tissue can be marked (step 45).

In the case of the example embodiment illustrated here, the mask is a binary mask, which means that a decision is made on the basis of the MRI data record and a threshold as to whether a voxel is considered to contain to fatty tissue or non-fatty tissue.

The mask is applied to the PET data record (step 47). As a result, those voxels in the PET data record are identified that correspond to fatty tissue. By way of example, the PET data record can then be modified to the effect that the PET signal of the voxels corresponding to fatty tissue is masked, attenuated and/or marked by any means such that they can be distinguished.

The PET data record modified thus is subsequently displayed to a user (step 49).

When displaying the PET data record, a user is made aware of whether the voxels that correspond to fatty tissue are displayed in a modified fashion or not. Furthermore, via the user interface, the user is provided with the option of setting the type of marking and/or the strength of the marking (step 51) him/herself.

FIG. 3 shows a further embodiment of a similar method according to an example of the invention.

In contrast to the embodiment shown in FIG. 2, the MRI data record is now used to generate a gradual mask that comprises a plurality of different mask values (step 45').

The mask values in this case correspond to the fat content of the voxels. The gradual mask is subsequently applied to the PET data record (step 47).

In this case, voxels in the PET data record with a higher fat content are masked to a greater degree than voxels in the PET data record that have a lower fat content.

Furthermore, via a user interface, the user is provided with the option of setting the degree of the masking of the voxels in the PET data record (step 51).

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

11 MRI/PET scanner
13 MRI unit
15 PET unit
17 PET detection units
19 LSO crystals
20 APD photodiode array
21 Electrical amplifier circuit
23 Control device
25 First partial apparatus
27 Second partial apparatus
29 Evaluation computer
31 Hybrid image
41 Step 41
43 Step 43
45 Step 45
45' Step 45'
47 Step 47
49 Step 49
51 Step 51

What is claimed is:

1. A method for recording and displaying medical imaging data records of a body part comprising fatty tissue, the method comprising:
    receiving, by a processor, an emission-tomographic data record and magnetic-resonance imaging data record of the body part, the emission-tomographic data record and the magnetic-resonance imaging data record being recorded by a combined positron-emission tomography (PET) and a magnetic resonance imaging device using a recording sequence designed such that the fatty tissue is displayable and distinguishable from other types of tissue;
    generating, by the processor, at least a gradual mask having a plurality of different values, each of the plurality of different values of the gradual mask corresponding to a voxel in the recorded magnetic-resonance imaging data record such that when fat content of one voxel is higher than fat content of another voxel in the recorded magnetic-resonance imaging data record, one of the plurality of different values of the gradual mask that correspond to the one voxel is higher than another one of the plurality of different gradual mask corresponding to the other voxel;
    identifying, by the processor, regions in the emission-tomographic data record using at least the generated gradual mask, the identified regions corresponding to the fatty tissue;
    modifying, by the processor, the emission-tomographic data record in the identified regions corresponding to the fatty tissue; and
    displaying the modified emission-tomographic data record to a user.

2. The method as claimed in claim 1, wherein the recording sequence is a recording sequence in which voxels are characterized by intensity values, with the intensity values constituting a measure for fat content of the body regions that correspond to the voxels.

3. The method as claimed in claim 2, wherein the magnetic-resonance imaging data record and the emission-tomographic data record are recorded with a temporal overlap or directly one after the other.

4. The method as claimed in claim 1, wherein the magnetic-resonance imaging data record and the emission-tomographic data record are recorded with a temporal overlap or directly one after the other.

5. The method as claimed in claim 4, wherein the magnetic-resonance imaging data record and the emission-tomographic data record are recorded while the patient is in the same position.

6. The method as claimed in claim 1, wherein the generating further generates a binary mask.

7. The method as claimed in claim 6, wherein the identifying further identifies regions in the emission-tomographic data record using the generated binary mask.

8. The method as claimed in claim 1, wherein the modifying of the emission-tomographic data record comprises marking fatty-tissue regions in the emission-tomographic data record, the marking being carried out using the magnetic-resonance imaging data record.

9. The method as claimed in claim 8, wherein the marking comprises an attenuation of an emission-tomographic signal in the fatty-tissue regions compared to non-fatty-tissue regions.

10. A non-transitory computer readable medium including computer program product, the computer program product comprising instructions, which when executed on a computer device, cause the computer device to implement the method of claim 1.

11. A device for evaluating and displaying medical imaging data records of a body part comprising fatty tissue, the device comprising:
    a computer unit configured to,
        receive an emission-tomographic data record and a magnetic-resonance imaging data record of the body part, the emission-tomographic data record and the magnetic-resonance imaging data record being recorded by a combined positron-emission tomography (PET) and a magnetic resonance imaging device using a recording sequence designed such that the fatty tissue is displayable and distinguishable from other types of tissue,
        generate at least a gradual mask having a plurality of different values, each of the plurality of different values of the gradual mask corresponding to a voxel in the recorded magnetic-resonance imaging data record such that when fat content of one voxel is higher than fat content of another voxel in the recorded magnetic-resonance imaging data record, one of the plurality of different values of the gradual mask that correspond to the one voxel is higher that another one of the plurality of different values of the gradual mask corresponding to the other voxel,
        identify regions in the emission-tomographic data record using at least the generated gradual mask, the identified regions corresponding to the fatty tissue,
        modify the emission-tomographic data record in the identified regions corresponding to the fatty tissue, and
        display the modified emission-tomographic data record to a user.

12. The device as claimed in claim 11, wherein the computer unit is further configured to generate a binary mask.

13. The device as claimed in claim 12, wherein the computer unit is further configured to identify regions in the emission-tomographic data record using the generated binary mask.

* * * * *